(12) United States Patent
Ruiz (10) Patent No.: US 6,261,273 B1
(45) Date of Patent: *Jul. 17, 2001

(54) ACCESS SYSTEM FOR BRANCHED VESSELS AMD METHODS OF USE

(76) Inventor: Carlos E. Ruiz, 1747 N. Country La., Pasadena, CA (US) 91107

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/074,568

(22) Filed: May 7, 1998

(51) Int. Cl.[7] .................................................. A61M 25/00
(52) U.S. Cl. ............................................ 604/284; 604/523
(58) Field of Search .............................. 604/96, 102, 284, 604/913, 535, 523; 606/191–195; 623/1; 128/898

(56) References Cited

U.S. PATENT DOCUMENTS

| | | | |
|---|---|---|---|
| 4,774,949 | * 10/1988 | Fogarty | 128/348.1 |
| 4,905,667 | * 3/1990 | Foerster et al. | 128/4 |
| 4,909,258 | * 3/1990 | Kuntz et al. | 128/658 |
| 5,443,500 | 8/1995 | Sigwart | 623/1 |
| 5,613,980 | 3/1997 | Chauhan | 606/194 |
| 5,643,340 | * 7/1997 | Nunokawa | 623/1 |
| 5,653,743 | * 8/1997 | Martin | 623/1 |
| 5,709,713 | * 1/1998 | Evans et al. | 623/1 |
| 5,720,735 | 2/1998 | Dorros | 604/284 |
| 5,906,640 | * 5/1999 | Penn et al. | 623/1 |

* cited by examiner

Primary Examiner—Richard K. Seidel
Assistant Examiner—Michael J Hayes
(74) Attorney, Agent, or Firm—Fish & Neave; Nicola A. Pisano (57) ABSTRACT

An access system is provided comprising a main tubular member having one or more lateral openings and a branch segment or secondary tubular member configured to be disposed through the lateral openings. The main tubular member is positioned in a vessel so that the openings are aligned with branches of the vessel. A secondary tubular member, or one or more branch segments, are then extended through the openings and into the branches to provide access for the delivery of therapeutic devices. Methods of deploying the access system to treat bifurcated or multi-branched vessels are also provided.

22 Claims, 6 Drawing Sheets

ACCESS SYSTEM FOR BRANCHED VESSELS AMD METHODS OF USE

FIELD OF THE INVENTION

The present invention relates to apparatus and methods for delivering a variety of medical devices, such as angioplasty balloons or stents to a precise position within a vessel through a delivery sheath or catheter. More particularly, the present invention provides a delivery sheath or catheter that may be used to position medical devices within two or more branches of a branched vessel.

BACKGROUND OF THE INVENTION

Numerous introducer sheaths and catheter systems have been developed for the endovascular delivery of a variety of medical devices, such as stents or angioplasty balloons. Typically, a guide wire is introduced into a vessel and advanced through the vasculature to a treatment site. A catheter is then advanced over the guide wire so that the distal end of the catheter is located at the treatment site. The catheter then may be used to transport and place any of a variety of medical devices or tools, such as stents, grafts, angioplasty balloons, atherectomy devices, etc., at the treatment site. The success of many minimally invasive medical procedures relies on the ability to precisely position such a catheter or sheath within a diseased vessel.

Endovascular procedures, such as angioplasty, may be complicated if the treatment site is near a bifurcation in a vessel. Complications may arise if, for example, one branch of the vessel will become closed or narrowed when an angioplasty balloon is inflated in the other branch.

It may also be necessary to treat both branches of a bifurcated vessel. For instance, when inserting a stent or graft in a bifurcated vessel to strengthen a diseased region of the vessel that spans both branches of the vessel, multiple stents may be required. Although such a procedure may be performed using previously known endovascular delivery apparatus and methods, the procedure may be difficult and time consuming, as it may be necessary to separately reinsert the catheter to place each of the stents.

Several prior catheter systems have attempted to address these difficulties. U.S. Pat. No. 5,720,735 to Dorros, for example, shows a catheter having a distal end with two branches. Two guide wires are used to deploy the branches of the distal end of the catheter into the two branches of a bifurcated vessel. A similar bifurcated catheter is shown in U.S. Pat. No. 5,613,980 to Chauhan.

A disadvantage of such previously known bifurcated access systems is that both branches of such systems are advanced through the vasculature simultaneously. Consequently, the delivery profile of such previously known devices may be quite large, herein the width of the distal end of the catheter is at least as wide as the combined diameters of the branching portions of the catheter. Consequently, access to narrow vessels is expected to be limited.

Additionally, if the region being treated with the previously known systems described in the aforementioned patents includes multiple branches, it may be necessary to repeatedly reinsert and reposition such catheter systems to treat all of the branches of the vasculature.

In view of the above, it would be desirable to provide apparatus and methods that permit rapid delivery and positioning of a medical device at a bifurcation in a vessel with an access device having a reduced delivery profile compared to previously known systems.

It would also be desirable to provide apparatus and methods that permit rapid delivery or positioning of a medical device within multiple branches of a vessel.

SUMMARY OF THE INVENTION

It is an object of the present invention to provide apparatus and methods that permit rapid and accurate placement of a medical device in either or both branches of a bifurcated vessel.

It is another object of this invention to provide apparatus and methods that have a delivery profile only slightly larger than the width of the individual branches of the vessel.

It is a still further object of the present invention to provide apparatus and methods that permit rapid delivery and placement of a medical device within any one of multiple branches of a vessel having multiple branches.

These and other objects of the present invention are accomplished by providing a main tubular member having one or more openings disposed on a lateral surface near a distal end of the member. The main tubular member is positioned in a vessel so that the openings are aligned with branches of the vessel. A secondary tubular member, or one or more branch segments, are then extended through the openings and into the branches.

In one embodiment, the main tubular member is first positioned in one branch of a multi-branch vessel, and one or more branch segments are advanced down the main tubular member and extended through the openings into the branches of the vessel. Each branch segment has a flexible flange disposed at its proximal end and a diameter only slightly narrower than the diameter of the main tubular member. The flange permits the length of the branch segment to pass through one of the openings in the main tubular member, but prevents the proximal end of the branch segment from passing through the opening. By providing a branch segment for each of the branches of the vessel, a multi-branch sheath or catheter may be constructed in situ, and then used to deliver and position a variety of medical devices.

In an alternative embodiment, after the main tubular member is positioned in one branch of the vessel, a secondary tubular member is advanced through the main tubular member and extended through one of the openings into a branch of the vessel. The secondary tubular member may then be used to deliver or place medical devices within the branch of the vessel. After treatment of the branch is completed, the secondary member may be repositioned to extend through another opening to treat another branch, or repositioned to extend through the distal end of the main tubular member. The diameter of the secondary tubular member need be only slightly smaller than the diameter of the main tubular member. Alternatively, the secondary tubular member may include a lateral opening at a predetermined distance from its distal end that is aligned with the lumen of the main tubular branch, thereby providing access to both branches simultaneously.

BRIEF DESCRIPTION OF THE DRAWINGS

Further features of the invention, its nature and various advantages will be more apparent from the accompanying drawings and the following detailed description of the preferred embodiments, in which.

DETAILED DESCRIPTION OF THE INVENTION

Figure 1:
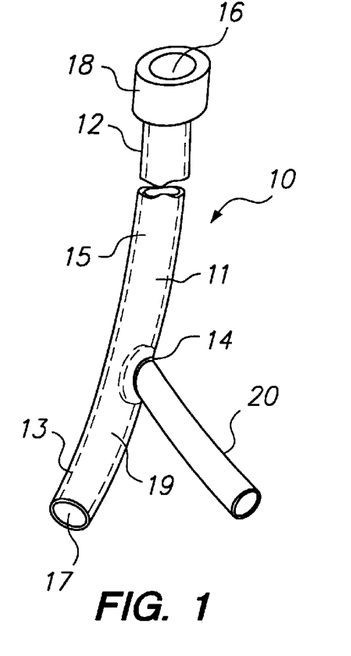
FIG. 1 is a perspective view of an illustrative embodiment of the apparatus of the present invention.

Referring to FIG. 1, apparatus 10 constructed in accordance with the present invention is described. Apparatus 10 comprises main tubular member 11 having proximal end 12, which is disposed outside a patient's body, and distal end 13, which is disposed in a main or branch vessel of the patient's vasculature. Branch segment 25 extends through lateral opening 14 of main tubular branch 11 and into a branch of the patient's vasculature. Therapeutic devices, such as dilatation balloons or stent delivery systems, thus may be disposed in the patient's vasculature through either the main tubular member or a branch segment.

In one embodiment, apparatus 10 has a length of several centimeters, and be used as an introducer sheath for bifurcated vessels. Alternatively, apparatus 10 may be several meters in length, and serves as an endovascular delivery catheter, for example, for use with stent delivery systems or angioplasty systems. Accordingly, the following written description is intended to apply equally to introducer sheaths and catheter systems.

Figures 2, 3:
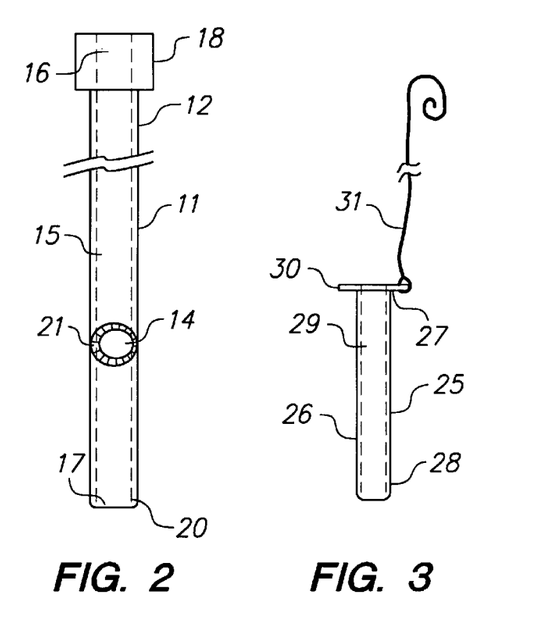
FIG. 2 is a side view of an illustrative main tubular member constructed in accordance with the present invention.
FIG. 3 is a side view of a branch segment constructed in accordance with the present invention.

Referring now to FIGS. 2 and 3, main tubular member 11 has lumen 15 extending from the proximal end 12 to distal end 13, and includes proximal opening 16 at the proximal end and distal opening 17 at the distal end. Main tubular member 11 preferably includes fitting 18 at proximal end 12 to facilitate introduction of guide wires and other devices into apparatus 10. Branch segment 25 is disposed through lateral opening 14 in lateral surface 19, near distal end 13, to provide access to a branch of a bifurcated vessel.

Endface 20 of distal opening 17 is preferably rounded to permit main tubular member 11 to be maneuvered through vessels without damaging the endothelial layer of the vessels. Main tubular member 11 preferably comprises a material commonly used in catheter construction, such as polyethylene, polyvinylchloride or polyurethane. In addition, main tubular member 11 may comprise ring 21 formed of a layer of radio-opaque marker material, such as gold, disposed surrounding lateral opening 14. Radio-opaque ring 21 may be employed to assist in orienting main tubular member 11 so that lateral opening 14 aligns with a branch of the vessel.

With respect to FIG. 2, branch segment 25 comprises tubular member 26 having proximal end 27, distal end 28, lumen 29 and flange 30. Lumen 29 extends between proximal end 27 and distal end 28. Pull-wire 31, which may comprise stainless steel, is coupled to proximal end 27 or flange 30, and is used to retrieve the branch segment upon completion of a procedure, as described hereinafter.

Like main tubular member 11, branch segment 25 preferably comprises a relatively soft material commonly used in catheter construction, such as polyethylene, polyvinylchloride or polyurethane. Flange 30 likewise comprises a flexible material, and is sufficiently flexible to pass through lumen 15 of main tubular member 11, but sufficiently rigid not to pass through lateral opening 14.

The diameter of branch segment 25 and flange 30 are such that branch segment 25 will easily pass through lumen 15 of main tubular member 11 and lateral opening 14, but flange 30 abuts against an interior surface of the main tubular member when branch segment 25 is positioned through lateral opening 14. To facilitate easy passage of branch segment 25 through lumen 15 of main tubular member 11, branch segment 25 preferably has a diameter at least two French smaller than the diameter of main tubular member 11.

Referring now to FIGS. 4A–4D, a multi-step process of deploying the apparatus of FIGS. 1 to 3 is described. First, a guide wire (not shown) is used to advance main tubular member 11 so that it extends from trunk vessel T into branch $B_1$ of a bifurcated vessel V. Main tubular member 11 may then be oriented using radio-opaque ring 21, visible under a fluoroscope, to position main tubular member 11 so that lateral opening 14 is aligned with branch $B_2$ of vessel V. The location of lateral opening 14 may be confirmed, for example, by injecting radio-opaque dye through fitting 18 of main tubular member 11.

Figure 4A:
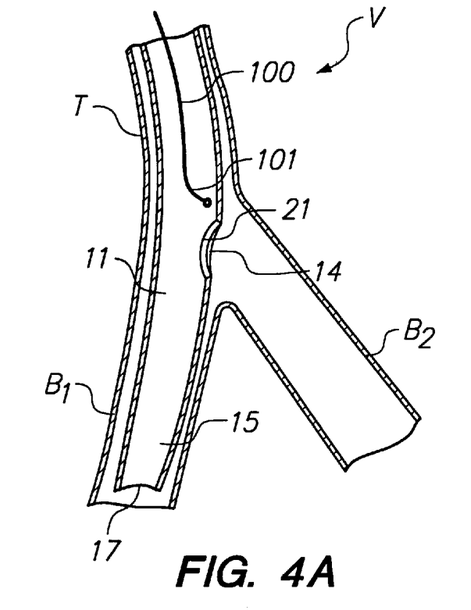
FIGS. 4A–4D illustrate the steps of deploying the apparatus of FIGS. 1–3 in a bifurcated vessel.
Figure 4B:
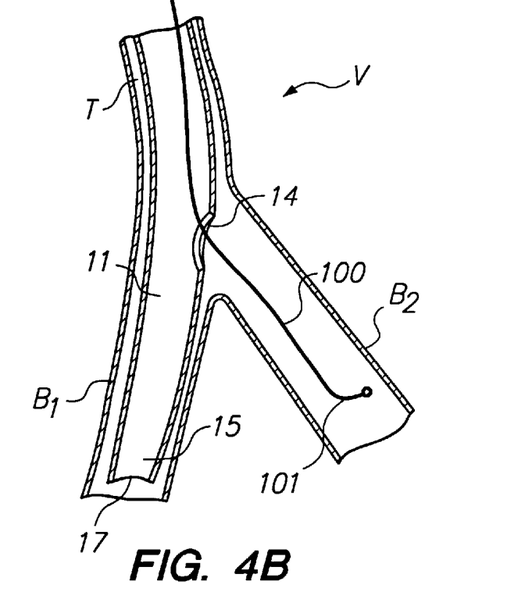

Guide wire 100, having ball-tipped and curved distal end portion 101, then is passed through main tubular member 11. Curved portion 101 causes guide wire 100 to follow the inside surface of lumen 15 of main tubular member 11 until it reaches lateral opening 14. When lateral opening 14 is reached, curved portion 101 causes guide wire 100 to exit lumen 15 through lateral opening 14 and project into branch $B_2$, as shown in FIG. 4B.

Figure 4C:
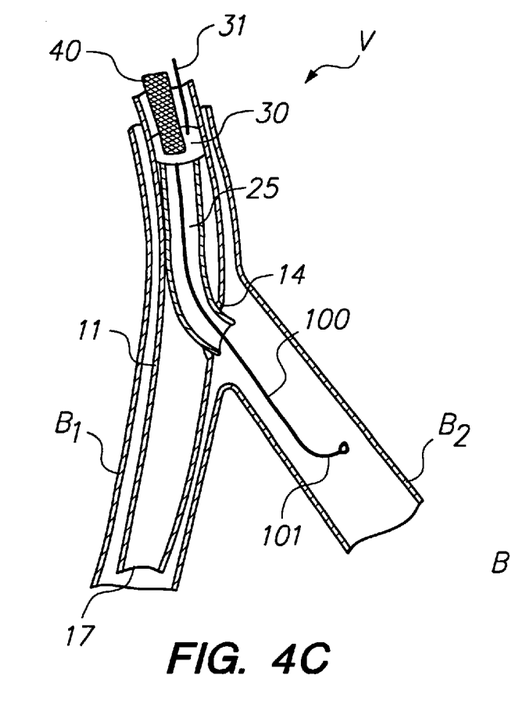

In FIG. 4C, push tube 40 is shown being used to push branch segment 25 along guide wire 100. Push tube 40 comprises a flexible hollow tube that engages and urges branch segment 25 along guide wire 100. When branch segment 25 reaches lateral opening 14, the branch segment 25 continues to follow guide wire 100 through lateral opening 14. Push tube 40 is used to urge flange 30 of branch segment 25 so that it abuts against the interior surface of lumen 15. Flange 30 prevents proximal end 27 of branch segment 25 from passing through lateral opening 14.

Figure 4D:
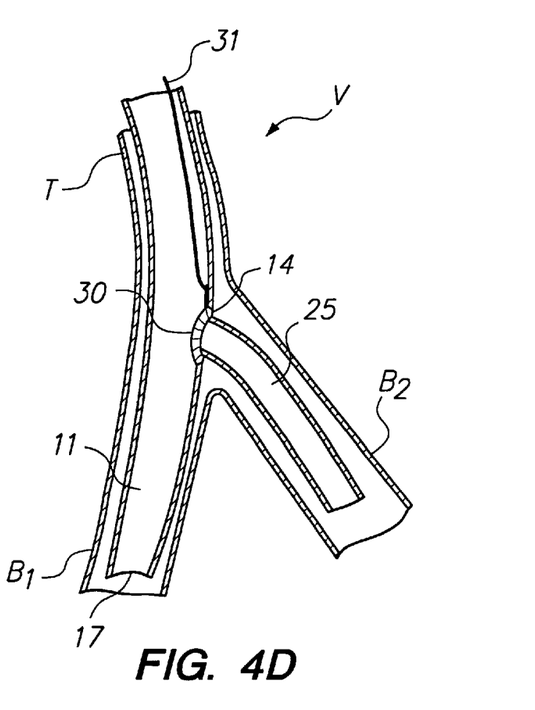

Once branch segment 25 is properly positioned, as is shown in FIG. 4D, guide wire 100 may be removed, or used to direct other devices into branch $B_2$. Because flange 30 projects only slightly from the interior surface of lumen 15, therapeutic devices also may be directed through distal opening 17 of main tubular member 11, thereby permitting access to branch $B_1$ of vessel V. Thus, the apparatus of FIG. 1 may be advantageously used to deliver and position therapeutic or other devices within either branch of a bifurcated vessel.

When work within vessel V is completed, apparatus 10 is removed by first removing branch segment 25. This is accomplished by pulling branch segment 25 back through main tubular member 11 using pull wire 31, the proximal end of which extends from fitting 18 of main tubular member 11. Once branch segment 25 has been removed, main tubular member 11 may be withdrawn from vessel V.

Figure 5:
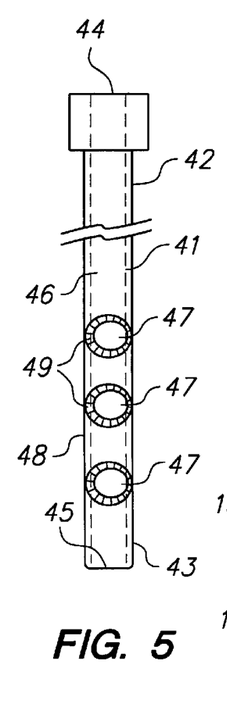
FIG. 5 is a side view of an alternative embodiment of the main tubular member of the present invention with multiple lateral openings for use in treating multiple branches of a vessel.

With respect to FIG. 5, an alternative embodiment of the main tubular member constructed in accordance with the present invention is described. Main tubular member 41 includes proximal end 42, distal end 43, proximal and distal openings 44 and 45, respectively, communicating with lumen 46, and plurality of lateral openings 47 in lateral surface 48. Each lateral opening 47 may include a radio-opaque ring 49 as described hereinabove with respect to the embodiment of FIGS. 1 and 2. Main tubular member 41 provides simultaneous access to multiple branches of a multi-branched vessel.

Figure 6A:
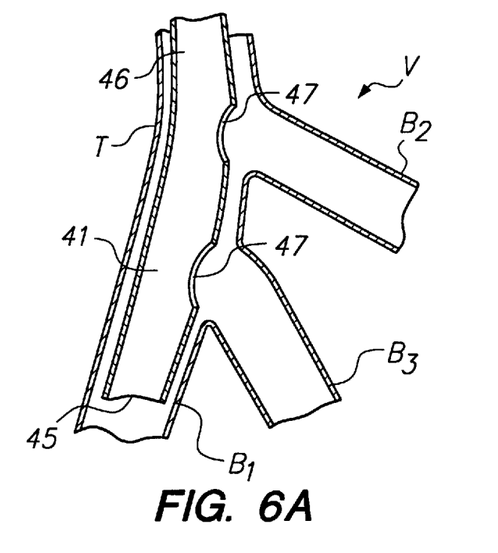
FIGS. 6A–6C illustrate steps of deploying the apparatus of FIGS. 3 and 5 in a multi-branched vessel.
Figure 6B:
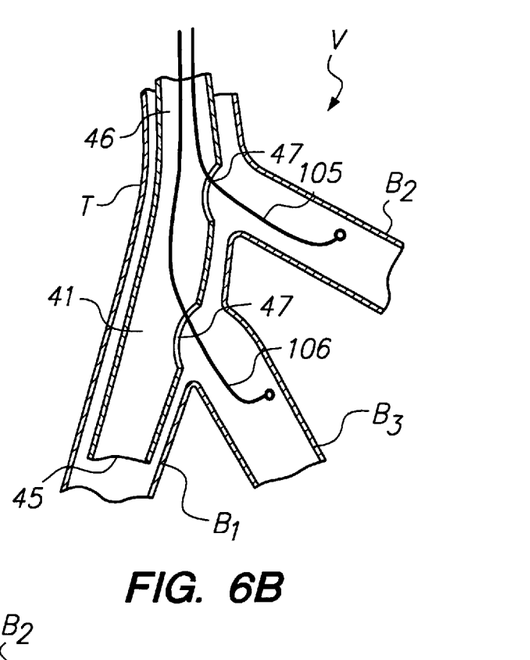

Referring to FIGS. 6A–6C, a multi-step deployment process for an apparatus comprising main tubular member 41 and a plurality of branch segments 25 is described. As shown in FIG. 6A, main tubular member 41 is positioned in trunk T of vessel V so that distal end 43 extends into branch $B_1$ and lateral openings 47 are aligned with branches $B_2$ and $B_3$. Guide wires 105 and 106 are then directed through main tubular member 41 so that they extend out of a respective one of the plurality of lateral openings 47 into branches $B_2$ and $B_3$, as shown in FIG. 6B. Pull wires 31 of the each of the branch segments extend to proximal end 42 of main tubular member 41.

Figure 6C:
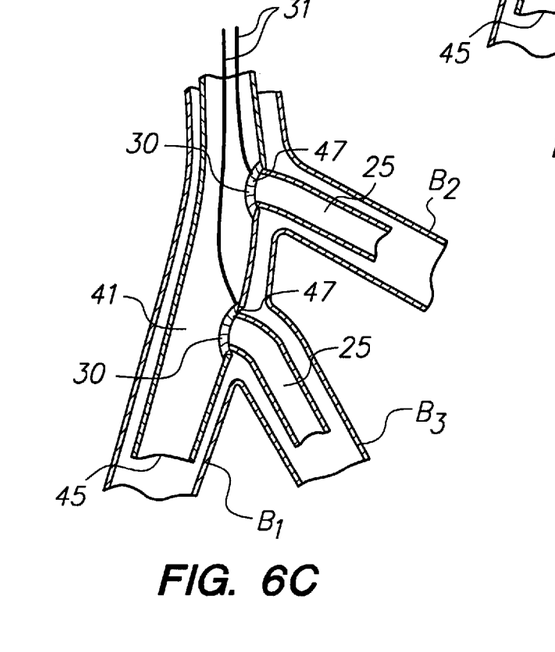

A push tube (see FIG. 4C) is then used to individually position a plurality of branch segments 25 through lateral openings 47, resulting in the multi-branched access system depicted in FIG. 6C. Because the flanges of each of branch segments 25 project only slightly into lumen 46 of main tubular member 41, simultaneous access is provided to each of branches $B_1$, $B_2$ and $B_3$. As described hereinabove, when work in vessel V is completed, branch segments 25 are first withdrawn using pull wires 31, and then main tubular member 41 is removed.

It will be evident to one skilled in the art that lateral openings 47 in main tubular member 41 must be positioned to align with the branch vessels to be treated. Thus, lateral openings 47 may have positions substantially different from those depicted in FIGS. 5 and 6A–6C. Similarly, the lengths and widths of the branch segments may be varied according to the specific requirements of the application for the access system is being employed.

Figure 7:
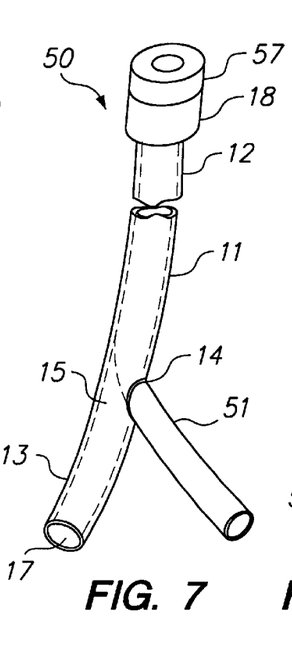
FIG. 7 is a perspective view of an alternative embodiment of the apparatus of the present invention.
Figure 8A:
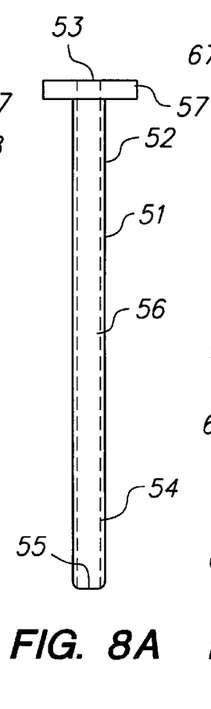
FIGS. 8A and 8B, are respectively, side views of a secondary tubular member employed in the apparatus of FIG. 7.

Referring now to FIGS. 7 and 8A, an alternative embodiment of the apparatus of the present invention is described. Apparatus 50 comprises main tubular member 11 of FIG. 2 and secondary tubular member 51, shown in FIG. 6. In accordance with this embodiment of the present invention, secondary tubular member 51 may be selectively positioned so that its distal end extends either through lateral opening 14 or through distal opening 17 of main tubular member 11.

With respect to FIG. 8A, secondary tubular member 51 has proximal end 52 with proximal opening 53, distal end 54 with distal opening 55, and lumen 56 coupling proximal opening 53 to distal opening 54. Proximal end 52 includes flange 57, which may be used to position secondary tubular member 51 relative to main tubular member 11. Distal end 54 may be positioned within either branch of a bifurcated vessel to permit therapeutic or other devices to be inserted in that branch via lumen 56. Secondary tubular member 51 also may be used in conjunction with main tubular member 41 to permit access to multiple branches of a branched vessel.

Secondary tubular member 51 has an outer diameter that permits it easily to pass through lumen 15 of main tubular member 11 and lateral opening 14, as shown in FIG. 7. To facilitate easy passage of secondary tubular member 51 through lumen 15, secondary tubular member 51 preferably has a diameter at least two French smaller than the diameter of main tubular member 11. Secondary tubular member 51 preferably comprises a soft, flexible material commonly used in catheter construction, such as polyethylene, polyvinylchloride, or polyurethane.

Deployment of an access system comprising main tubular member 41 and secondary tubular member 51 is described with respect to FIGS. 9A–9D. With respect to FIG. 9A, main tubular member 41 first is maneuvered into a position within vessel V so distal end 43 is positioned in branch $B_1$ and the plurality of lateral openings 47 are aligned with branches $B_2$ and $B_3$ of vessel V. Guide wire 107 is then inserted into main tubular member 41 so that it exits a selected one of the plurality of lateral openings 47, as determined, for example, by fluoroscopy.

Figure 9A:
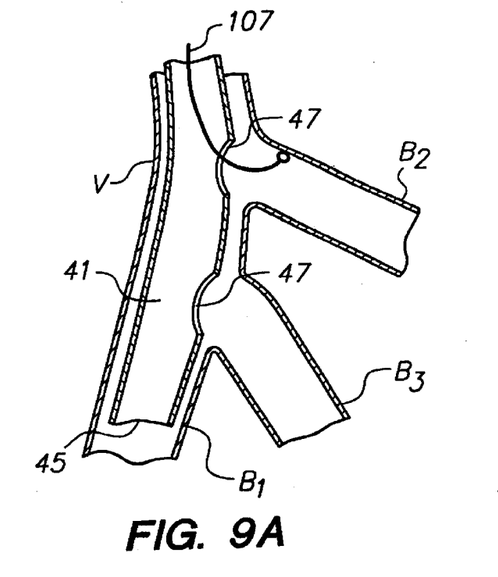
FIGS. 9A–9D illustrate steps of deploying the apparatus of FIGS. 5 and 8A to treat multiple branches of a multi-branched vessel.
Figure 9B:
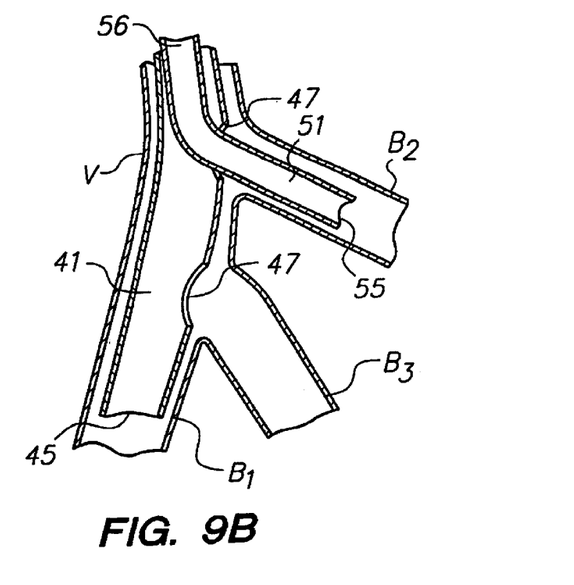
Figure 9C:
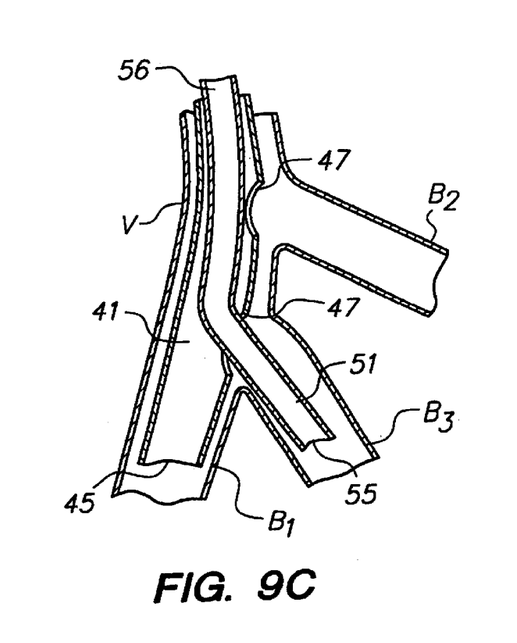

Secondary tubular member 51 is then advanced along guide wire 107 through lumen 46 of main tubular member 41 and through the selected one of the plurality of lateral openings 47. Secondary tubular member 51 is thus positioned within branch $B_2$ of vessel V, as shown in FIG. 9B. When work in branch $B_2$ is completed, secondary tubular member is withdrawn proximally until distal end 54 is retracted within lumen 46, and a guide wire extended through lumen 56 until it exits another lateral opening 47 and extends into branch $B_3$, as shown in FIG. 9C.

Figure 9D:
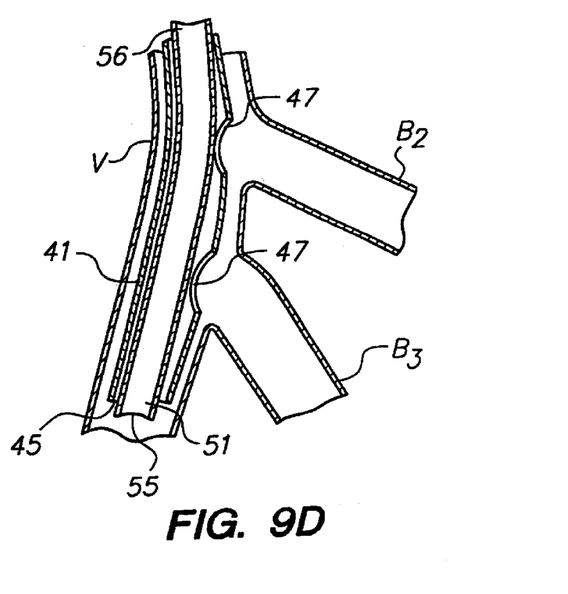

The foregoing steps may be repeated until all of the side branches of vessel V have been treated. Finally, as depicted in FIG. 9D, secondary tubular member 51 is directed through distal opening 45 of main tubular member 41, thereby allowing treatment of branch $B_1$. When treatment of all of the branches of vessel V is completed, secondary tubular member 51 and main tubular member 41 may be withdrawn together.

Although the use of secondary tubular member 51 does not provide simultaneous access to multiple branches of a multi-branched vessel, it overcomes some of the disadvantages of previously known access systems. For example, apparatus 50 is expected to provide a much smaller delivery profile than previously known systems.

In addition, because secondary tubular member 51 is repositioned within the lumen of the main tubular member, which remains stationary, apparatus 50 is expected to create less trauma to the endothelial layer of the vessel than would be expected if a single catheter or introducer sheath were to be removed and repeatedly repositioned. The use of a main tubular member having a plurality of lateral holes positioned to align with the branches in a vessel is expected to provide a significant time savings in the positioning of the secondary tubular member, as compared to repeatedly positioning a single catheter or introducer in each branch of a multi-branched vessel without use of the apparatus of the present invention.

Figure 8B:
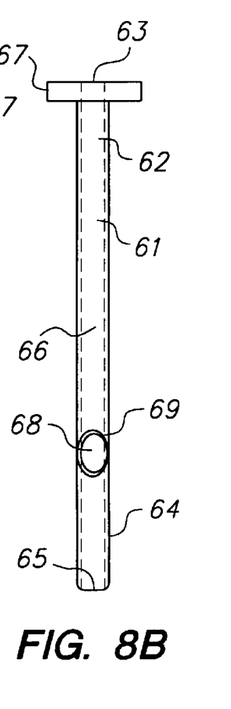

Referring now to FIG. 8B, a further alternative embodiment of a secondary tubular member suitable for use in the apparatus of FIG. 7 is described. Secondary tubular member 61 has proximal end 62 with proximal opening 63, distal end 64 with distal opening 65, and lumen 66 coupling proximal opening 63 to distal opening 65. Proximal end 62 includes flange 67, which may be used to position secondary tubular member 61 relative to main tubular member 11. Distal end 64 includes lateral opening 68 a predetermined distance from the distal end face of the secondary tubular member, depending upon the intended application of the apparatus.

Secondary tubular member 61 has an outer diameter that permits it easily to pass through lumen 15 of main tubular member 11 and lateral opening 14, as shown in FIG. 7. To facilitate easy passage of secondary tubular member 61 through lumen 15, secondary tubular member 61 preferably has a diameter at least two French smaller than the diameter of main tubular member 11. Secondary tubular member 61 preferably comprises a soft, flexible material commonly used in catheter construction, such as polyethylene, polyvinylchloride, or polyurethane.

Figure 10A:
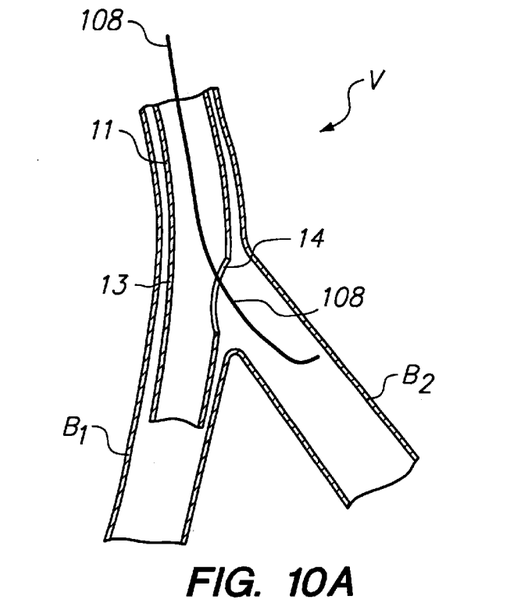
FIGS. 10A–10C illustrate steps of deploying the apparatus of FIGS. 5 and 8B to simultaneously provide access to both branches of a bifurcated vessel.

Deployment of an access system comprising main tubular member 11 and secondary tubular member 61 is described with respect to FIGS. 10A–10C. With respect to FIG. 10A, main tubular member 11 first is maneuvered into a position within vessel V so that distal end 13 is positioned in branch $B_1$ and lateral opening 14 1s aligned with branch $B_2$. Guide wire 108 is then inserted into main tubular member 11 so that it exits through lateral opening 14, as determined, for example, by fluoroscopy.

Figure 10B:
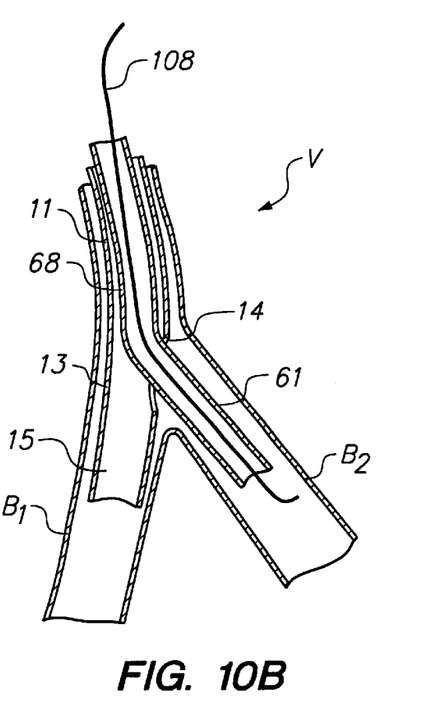

Secondary tubular member 61 is then advanced along guide wire 108 through lumen 15 of main tubular member 11 and through lateral opening 14 until lateral opening 68 in secondary tubular member 61 is aligned with lumen 15 of main tubular member 11. Secondary tubular member 61 may include radio-opaque ring 69 disposed surrounding lateral opening 68 to assist in aligning lateral opening 68 with lumen 15. Secondary tubular member 61 is thus positioned within branch $B_2$ of vessel V, as shown in FIG. 10B. Guide wire 109 is then inserted through lumen 66 of secondary tubular member 61 so that it passes through opening 68 and extends into branch $B_1$, as shown in FIG. 10C.

Figure 10C:
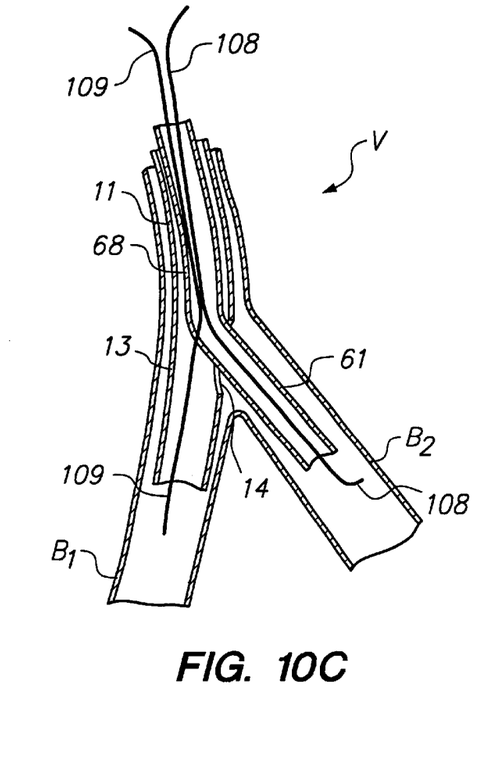

Accordingly, main tubular member 11 and secondary tubular member 61, when disposed in vessel V as illustrated in FIGS. 10A–10C, provide simultaneous access to branches $B_1$ and $B_2$. Therapeutic devices therefore may be advanced along either or both of guide wires 108 and 109 to treat the branches. When work is completed, guide wires 108 and 109 are removed, secondary tubular member is withdrawn proximally, and main tubular member 11 may then be withdrawn.

Alternatively, secondary tubular member 61 may be used with main tubular member 41 of FIG. 5 to serially treat several side branches, while providing access to at least one other branch. In this case, secondary tubular member 61 is repositioned after each side branch is treated.

Figure 11:
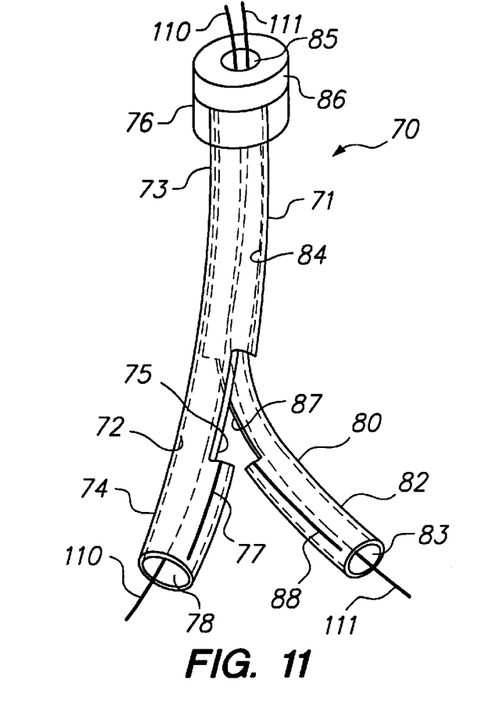
FIG. 11 is a side view of alternative embodiment of the apparatus of FIGS. 2 and 8B.

Referring now to FIG. 11, an alternative embodiment of the access system of FIGS. 2 and 8B is described. Access system 70 comprises main tubular member 71 having lumen 72 extending from proximal end 73 to distal end 74, rectangular lateral aperture 75 communicating with lumen 72. Proximal end 73 includes flange 76, while distal end 74 includes slit 77 extending from lateral aperture 75 to a point just proximal of opening 78.

Secondary tubular member 80 has a proximal end disposed within lumen 72 of main tubular member 71, distal end 82 with distal opening 83, and lumen 84 coupling proximal opening 85 to distal opening 83. The proximal end of secondary tubular member 80 includes flange 86, which may be used to position secondary tubular member 80 relative to main tubular member 71. Distal end 82 includes rectangular lateral opening 87 disposed a predetermined distance from the distal end face of the secondary tubular member, and includes slit 88 extending from lateral aperture 87 to a point just proximal of opening 83.

Secondary tubular member 80 has an outer diameter that permits it easily to pass through lumen 72 of main tubular member 71 and rectangular lateral opening 75. To facilitate easy passage of secondary tubular member 80 through lumen 72, secondary tubular member 80 preferably has a diameter at least two French smaller than the diameter of main tubular member 71. As for the other embodiments described hereinabove, main tubular member 71 and secondary tubular member 80 preferably comprises a soft, flexible material commonly used in catheter construction, such as polyethylene, polyvinylchloride, or polyurethane.

When secondary tubular member 80 is positioned in lumen 72 of main tubular member 71, distal end 82 projects through rectangular lateral opening 75, and opening 87 of secondary tubular member 80 is aligned with lumen 72. Accordingly, guidewire 110 may be deployed through lumen 84 of secondary tubular member 80 so that the distal end of guide wire 110 extends through opening 87 and into distal end 74 of main tubular member 71. Guidewire 111 is positioned in lumen 84 of secondary tubular member 80 so that it extends through distal opening 83 of the secondary tubular member. Slits 77 and 88 are provided to permit distal ends 74 and 82 to tear longitudinally, thereby enabling withdrawal of the access system after deployment of vascular prostheses in the branches of the vessel.

Figure 12A:
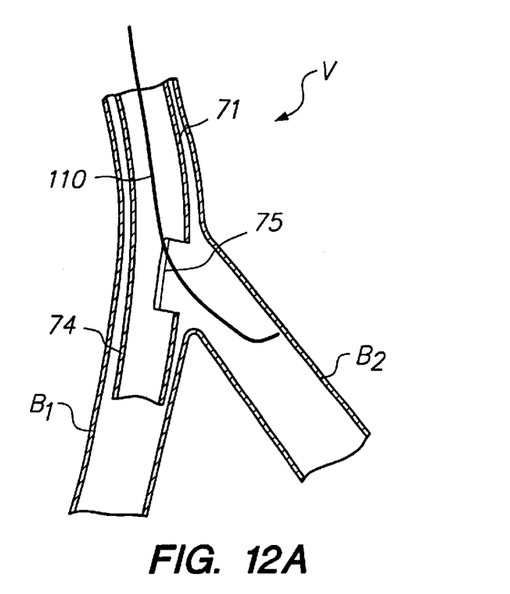
FIGS. 12A to 12C illustrate steps of employing the apparatus of FIG. 11 to deploy a pair of vascular prostheses.

Referring now to FIGS. 12A to 12C, use of access system 70 to deploy vascular prostheses, such as described in U.S. Pat. No. 5,443,500 to Sigwart, which is incorporated herein by reference, is described. With respect to FIG. 12A, main tubular member 71 first is maneuvered into a position within vessel V so that distal end 74 is positioned in branch $B_1$ and lateral opening 75 Is aligned with branch $B_2$. Guide wire 110 is then inserted into main tubular member 71 so that it exits through rectangular lateral opening 75, as determined, for example, by fluoroscopy.

Figure 12B:
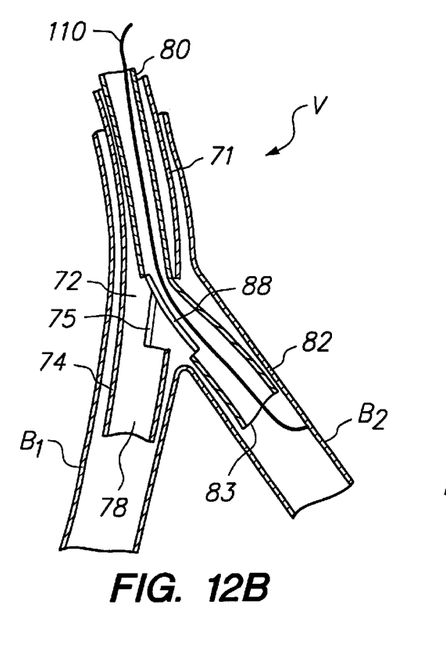

Secondary tubular member 80 is then advanced along guide wire 110 through lumen 72 of main tubular member 71 and through lateral opening 75 until lateral opening 87 in secondary tubular member 80 is aligned with lumen 72 of main tubular member 71. Secondary tubular member 80 may include a radio-opaque band (not shown) disposed surrounding lateral opening 87 to assist in aligning lateral opening 87 with lumen 72. Secondary tubular member 80 is therefore positioned within branch $B_2$ of vessel V, as shown in FIG. 12B. Guide wire 111 is then inserted through lumen 84 of secondary tubular member 80 so that it passes through opening 87 and extends into branch $B_1$, as depicted in FIG. 12C.

Figure 12C:
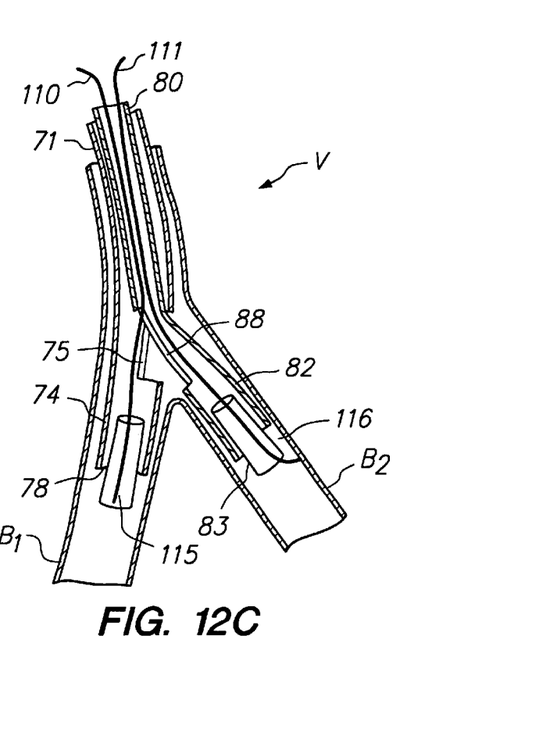

When main tubular member 71 and secondary tubular member 80 are disposed in vessel V as illustrated in FIGS. 12A–12C, simultaneous access is provided to branches $B_1$ and $B_2$. Previously known stent delivery devices, such as described in the above-incorporated Sigwart patent, may then be advanced along guidewires 110 and 111 to deploy stents 115 and 116 within branches $B_1$ and $B_2$ just distal of the bifurcation, as shown in FIG. 12C.

During deployment of stents 115 and 116, distal end 74 of main tubular member 71 and distal end 82 of secondary tubular member 80 may become trapped against the walls of the branches. In accordance with the present invention, however, slits 77 and 88 permit the material of the tubular members to tear longitudinally towards distal openings 78 and 83, respectively, when the tubular members are pulled proximally. Thus, access system enables a pair of vascular prostheses to be deployed within a bifurcated vessel while permitting easy withdrawal of the access system upon completion of the procedure.

While preferred illustrative embodiments of the invention are described above, it will be apparent to one skilled in the art that various changes and modifications may be made therein without departing from the invention, and the appended claims are intended to cover all such changes and modifications that fall within the true spirit and scope of the invention.

What is claimed is:

1. Apparatus for accessing each branch of a vessel having a plurality of branches, the apparatus comprising:

a main tubular member comprising a proximal end having a portion defining a proximal opening, a distal end having a portion defining a distal opening, a main lumen extending between the proximal opening and the distal opening, and a lateral surface having a lateral opening communicating with the main lumen;

a branch segment having a proximal end defining a first opening, a distal end defining a second opening, a branch lumen extending between the first and second openings, and a flange disposed adjacent the proximal end, the branch segment configured to pass through the main lumen and the lateral opening so that the flange abuts against an interior surface of the main tubular member; and a pull wire coupled to the proximal end of the branch segment.

2. The apparatus of claim 1 wherein the main tubular member further comprises a portion defining a plurality of lateral openings.

3. The apparatus of claim 2 further comprising a plurality of branch segments, each branch segment disposed in a corresponding one of the plurality of lateral openings.

4. The apparatus of claim 1 wherein the main tubular member comprises a material selected from the group consisting of polyethylene, polyurethane, and polyvinylchloride.

5. The apparatus of claim 1 wherein the main tubular member had a first diameter and the branch segment has a second diameter, the second diameter at least two French smaller than the first diameter.

6. The apparatus of claim 1 further comprising a radio-opaque ring surrounding the lateral opening, the radio-opaque ring assisting in orienting the main tubular member so that the lateral opening aligns with a branch of the vessel.

7. A guide catheter for transluminally accessing each branch of a vessel having a plurality of branches, the apparatus comprising:

a main tubular member adapted to be removably disposed in a vessel, the main tubular member comprising a proximal end having a portion defining a proximal opening, a distal end having a portion defining a distal opening, a main lumen extending between the proximal opening and the distal opening, and a lateral surface having a preformed lateral opening of predetermined size that communicates with the main lumen, the lateral opening not extending to the distal end and distal opening; and a secondary tubular member having a proximal end defining a first opening, a distal end defining a second opening, and a secondary lumen extending between the first and second openings, the secondary lumen sized to permit interventional devices to be passed therethrough, the secondary tubular member configured to be removably extended through the main lumen after placement of the main tubular member within the vessel with the preformed lateral opening in registration with a selected one of the plurality of branches, so that the secondary tubular member may be selectively extended through either the preformed lateral opening or the distal opening.

8. The apparatus of claim 7, wherein the main tubular member further comprises a portion defining a plurality of lateral openings.

9. The apparatus of claim 8 further comprising a radio-opaque ring surrounding the lateral opening, the radio-opaque ring assisting in orienting the main tubular member so that the lateral opening aligns with a branch of the vessel.

10. The apparatus of claim 7, wherein the secondary tubular member further comprises a portion defining a lateral opening.

11. The apparatus of claim 10 further comprising a radio-opaque ring surrounding the lateral opening in the secondary tubular member, the radio-opaque ring assisting in orienting the lateral opening in the secondary tubular member with the lumen of the main tubular member.

12. The apparatus of claim 10, wherein the preformed lateral openings of the main tubular member and secondary tubular member are rectangular.

13. The apparatus of claim 7, wherein the main tubular member comprises a material selected from the group consisting of polyethylene, polyurethane, and polyvinylchloride.

14. The apparatus of claim 7, wherein the main tubular member has a first diameter, the secondary tubular member has a second diameter and the second diameter is at least two French smaller than the first diameter.

15. A method of deploying a guide catheter in a vessel comprising:

providing a main tubular member comprising a proximal end having a portion defining a proximal opening, a distal end having a portion defining a distal opening, a main lumen extending between the proximal opening and the distal opening, and a lateral surface having a preformed lateral opening of predetermined size that communicates with the main lumen;

providing a branch segment having a proximal end defining a first opening, a distal end defining a second opening, a branch lumen extending between the first and second openings, a flange disposed adjacent the proximal end, and a pull wire coupled to the flange;

transluminally advancing the main tubular member within a vessel so that the lateral opening is aligned with a branch of the vessel; and after transluminally advancing the main tubular member within the vessel, inserting the branch segment transluminally through the main lumen so that the branch segment extends through the preformed lateral opening into the branch of the vessel, and the flange abuts against an interior surface of the main tubular member;

after completing an interventional procedure, pulling on the pull wire to withdraw the branch segment from the main lumen of the main tubular member; and withdrawing the main tubular member from the vessel.

16. The method of claim 15, wherein inserting the branch segment transluminally through the main tubular member comprises:

directing a guide wire through the main tubular member and the lateral opening into the branch of the vessel; and urging the branch segment along the guide wire.

17. The method of claim 15, wherein the branch segment further comprises a pull wire coupled to the branch segment, the method further comprising, upon completion of treatment to the vessel, a step of pulling the pull wire to remove the branch segment from the main lumen.

18. The method of claim 15, wherein the vessel has multiple branches, the main tubular member comprises a plurality of preformed lateral openings, and transluminally advancing the main tubular member and inserting the branch segment further comprise:

transluminally advancing the main tubular member so that more than one of the plurality of preformed lateral openings are aligned with corresponding ones of the branches of the vessel; and inserting a plurality of branch segments transluminally through the main lumen so that each one of the plurality of branch segments extends through a corresponding one of the plurality of preformed lateral openings into one of the branches of the vessel.

19. A method of deploying an access system comprising:

providing a main tubular member comprising a proximal end having a portion defining a proximal opening, a distal end having a portion defining a distal opening, a main lumen extending between the proximal opening and the distal opening, and a lateral surface having a preformed lateral opening of predetermined size that communicates with the main lumen;

providing a secondary tubular member having a proximal end defining a first opening, a distal end defining a second opening, and a secondary lumen extending between the first and second openings;

transluminally advancing the main tubular member within a vessel so that the preformed lateral opening is aligned with a first branch of the vessel;

after transluminally advancing the main tubular member within the vessel, inserting the secondary tubular member transluminally through the main lumen and the preformed lateral opening so that the secondary tubular member extends into the first branch of the vessel;

upon completion of treatment in the first branch, withdrawing the secondary tubular member from the first branch; and extending the secondary tubular member through the distal opening of the main tubular member into a second branch of the vessel.

20. The method of claim 19, wherein inserting the secondary tubular member through the preformed lateral opening further comprises:

advancing a guide wire through the main lumen and the preformed lateral opening of the main tubular member, and positioning the guide wire within the first branch of the vessel; and advancing the secondary tubular member along the guide wire.

21. The method of claim 19, wherein the vessel has multiple branches, the main tubular member comprises a portion defining a plurality of preformed lateral openings, and transluminally advancing the main tubular member comprises transluminally advancing the main tubular member so that at least some of the plurality of preformed lateral openings are aligned with corresponding ones of the multiple branches, the method further comprising sequentially inserting the secondary tubular member through the at least some of the plurality of the preformed lateral openings.

22. The method of claim 21, wherein sequentially directing the secondary tubular member through the at least some of the plurality of the preformed lateral openings further comprises sequentially advancing a guide wire through the at least some of the preformed lateral openings, and advancing the secondary tubular member along the guide wire.

* * * * *